, 21 Drawing Sheets

(12) United States Patent
DiRisio et al.

(10) Patent No.: US 8,876,379 B2
(45) Date of Patent: Nov. 4, 2014

(54) COLLAPSIBLE COLUMN MOVEMENT APPARATUS FOR MOBILE X-RAY DEVICE

(75) Inventors: Anthony DiRisio, Rochester, NY (US); Joseph E. Stagnitto, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 416 days.

(21) Appl. No.: 13/083,785

(22) Filed: Apr. 11, 2011

(65) Prior Publication Data

US 2011/0249807 A1 Oct. 13, 2011

Related U.S. Application Data

(60) Provisional application No. 61/323,503, filed on Apr. 13, 2010.

(51) Int. Cl.
| | | |
|---|---|---|
| H05G 1/02 | (2006.01) | |
| H05G 1/00 | (2006.01) | |
| A61B 6/00 | (2006.01) | |

(52) U.S. Cl.
CPC .............. *A61B 6/4405* (2013.01); *A61B 6/447* (2013.01)
USPC ............................ 378/198; 378/193; 378/197

(58) Field of Classification Search
USPC ............. 378/55, 91, 193, 194, 196–198, 204, 378/205, 210
See application file for complete search history.

(56) References Cited

U.S. PATENT DOCUMENTS

| | | | |
|---|---|---|---|
| 2,041,242 A | 5/1936 | Goldfield .................. 248/123 |
| 4,341,279 A | 7/1982 | Waerve ........................ 180/19 |
| 4,716,581 A | 12/1987 | Barud ........................... 378/198 |
| 4,989,229 A * | 1/1991 | Negrelli et al. ............... 378/198 |
| 5,067,145 A * | 11/1991 | Siczek et al. ................... 378/198 |
| 5,388,142 A * | 2/1995 | Morris ........................... 378/198 |
| 5,425,069 A | 6/1995 | Pellegrino et al. |
| 5,475,730 A | 12/1995 | Galando ....................... 378/157 |
| 5,499,284 A * | 3/1996 | Pellegrino et al. ........... 378/198 |
| 5,544,217 A * | 8/1996 | Kadowaki et al. ............ 378/198 |
| 6,193,415 B1 | 2/2001 | Kadowaki et al. ............ 378/198 |
| 6,217,214 B1 * | 4/2001 | Cabral et al. .................. 378/196 |
| 6,237,707 B1 * | 5/2001 | Lyke et al. .................... 180/19.3 |
| 6,851,853 B2 | 2/2005 | Nakagawa et al. ........... 378/197 |
| 7,016,467 B2 | 3/2006 | Brooks ......................... 378/102 |
| 2003/0190014 A1 | 10/2003 | Nakagawa et al. |

FOREIGN PATENT DOCUMENTS

| | | |
|---|---|---|
| JP | 2005-073710 | 3/2005 |
| WO | 90/14748 | 11/1990 |

OTHER PUBLICATIONS

International Search Report & Written Opinion, International application No. PCT/US2011/032026, dated Dec. 12, 2011, 8 pages.

* cited by examiner

*Primary Examiner* — Anastasia Midkiff

(57) ABSTRACT

A mobile radiography apparatus has a portable transport frame and a sectioned vertical column mounted on the frame and defining a vertical axis and having a base section having a fixed vertical position relative to the vertical axis and at least one movable section that is translatable to a variable vertical position along the vertical axis. A counterbalance apparatus is coupled to the at least one movable section of the vertical column with an actuator that is energizable to translate the at least one movable section along the vertical axis. A boom apparatus supports an x-ray source and is coupled to the at least one movable section for vertical displacement of the boom apparatus to a height position. A height sensing element provides a signal that is indicative of the height position of the boom apparatus.

10 Claims, 21 Drawing Sheets

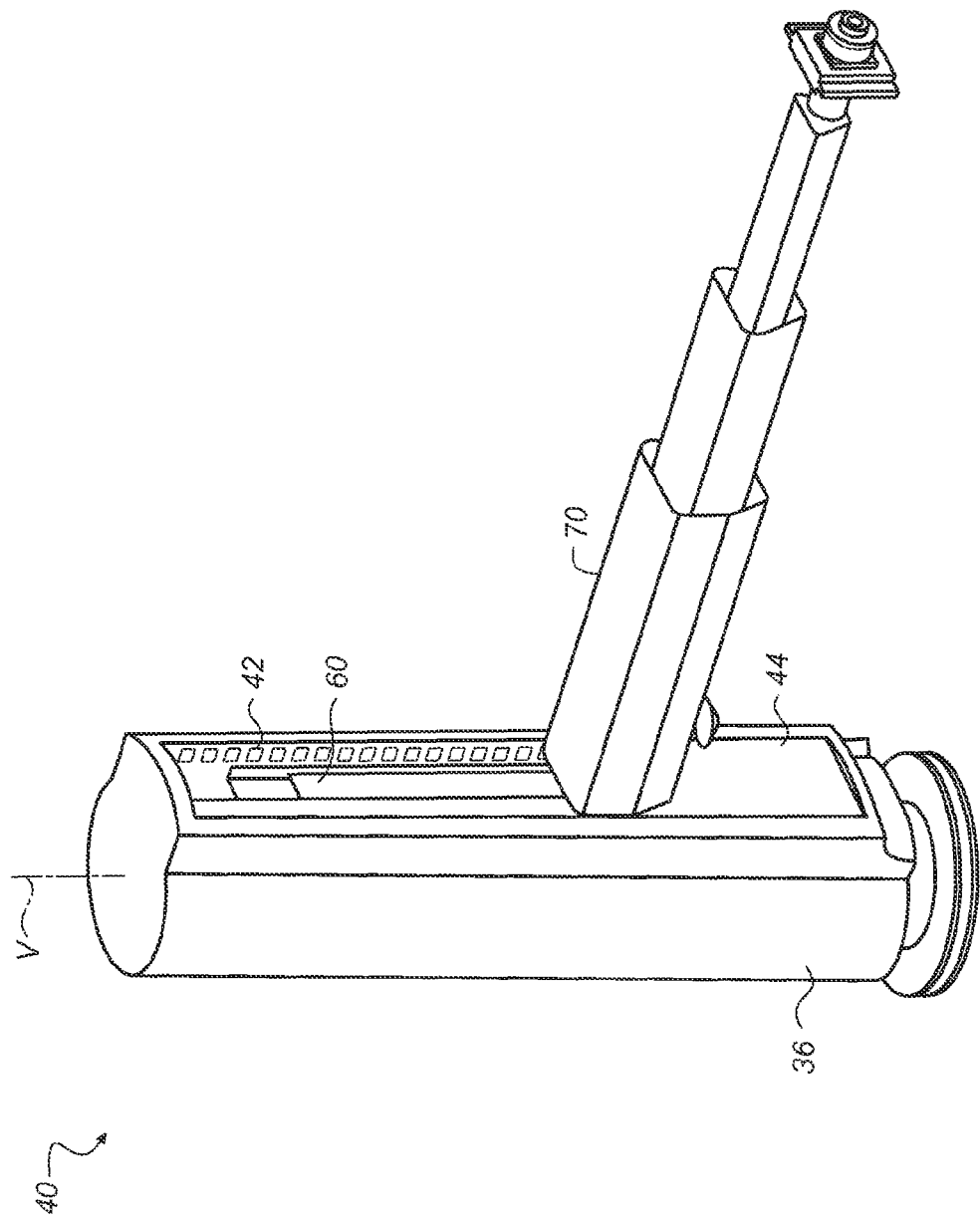

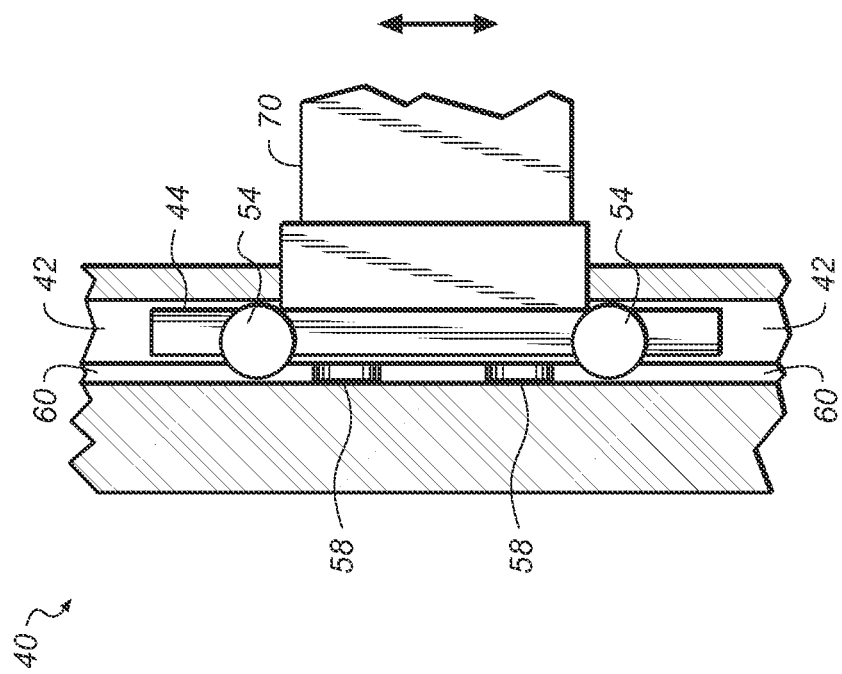
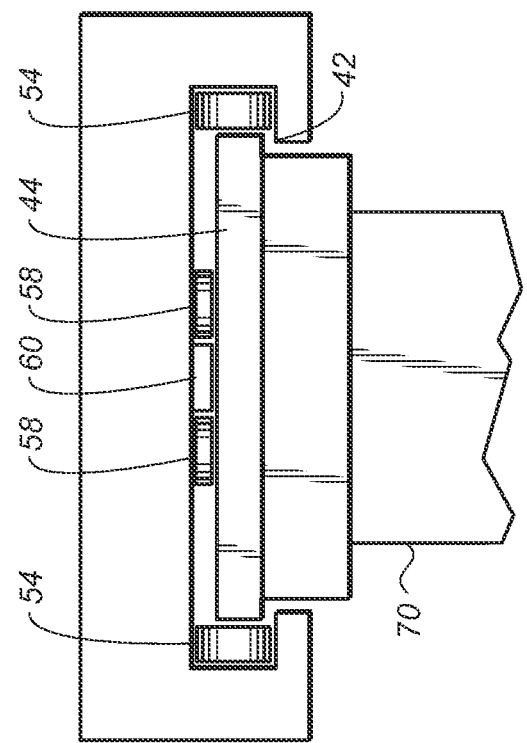
FIG. 14A
FIG. 14B

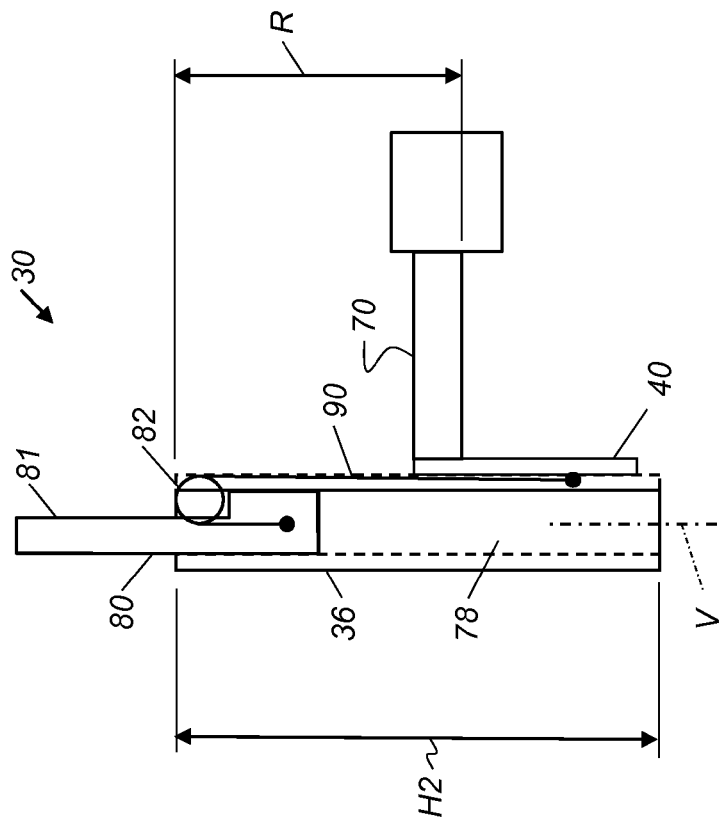
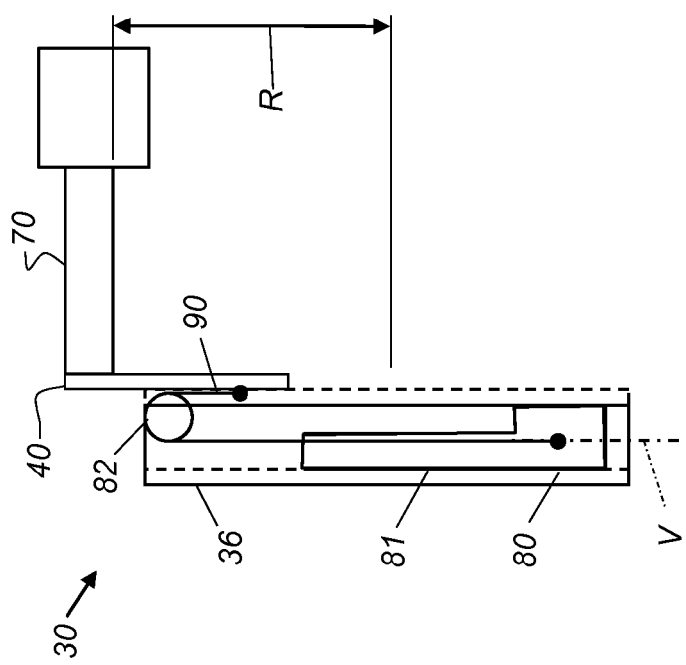

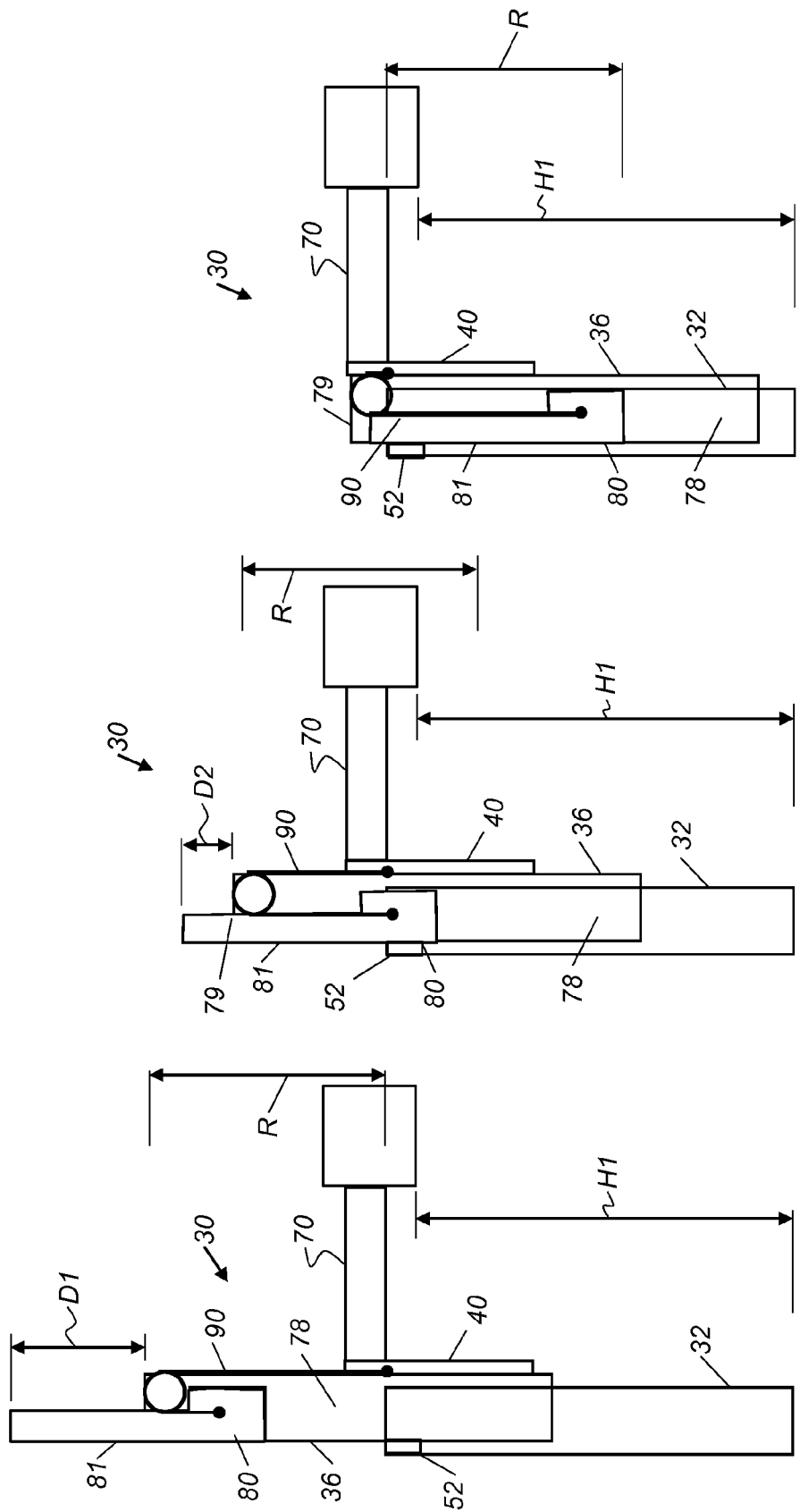

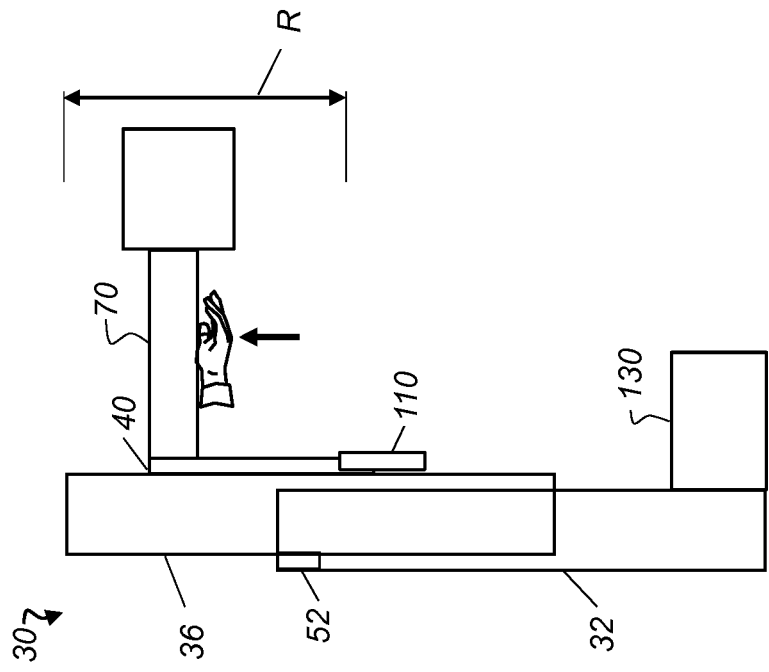
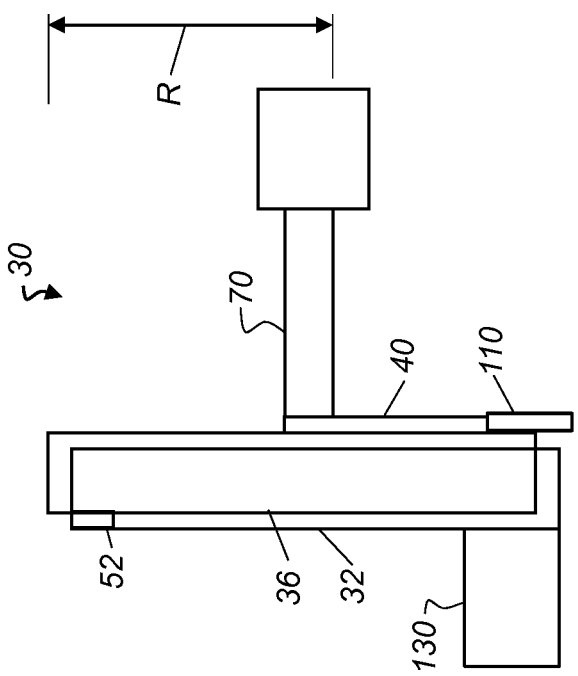
FIG. 19B
FIG. 19A

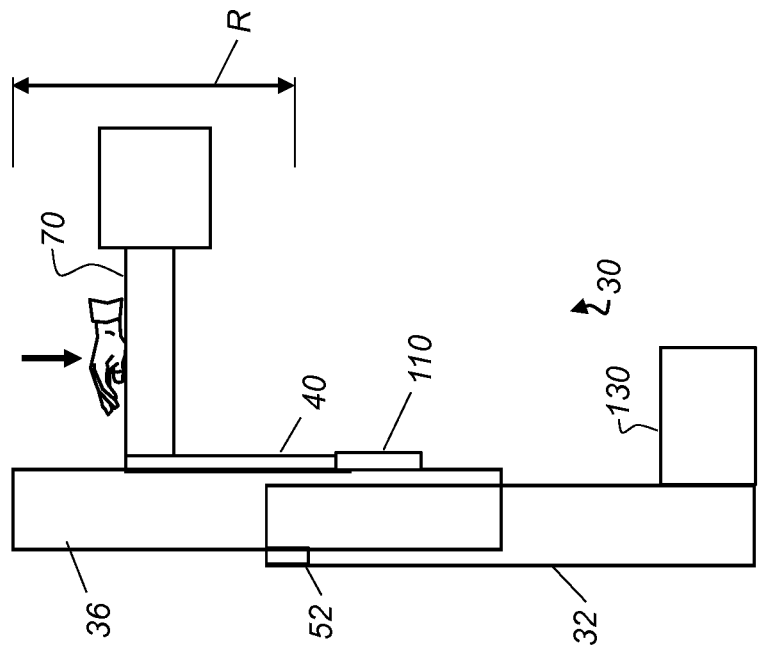
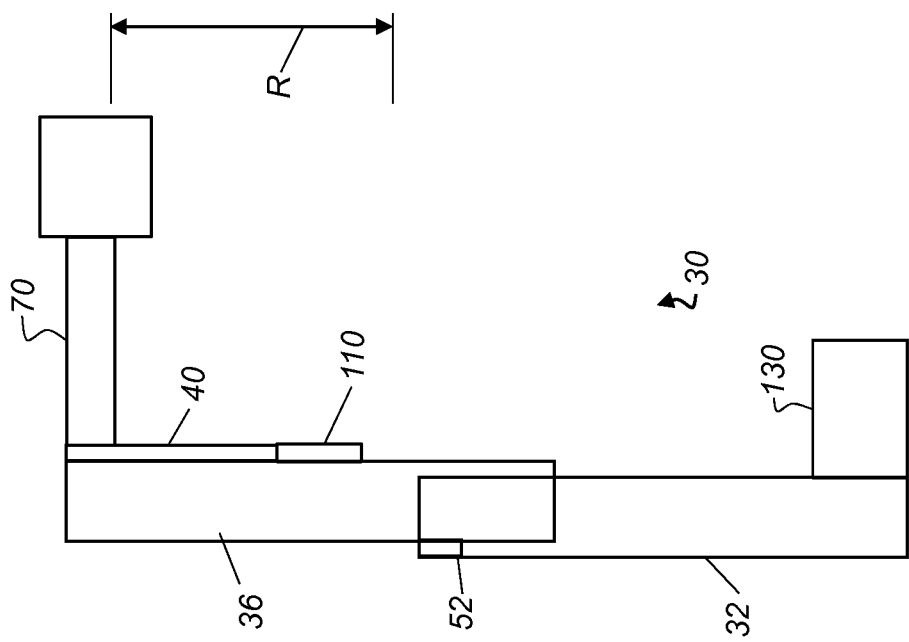

COLLAPSIBLE COLUMN MOVEMENT APPARATUS FOR MOBILE X-RAY DEVICE

CROSS REFERENCE TO RELATED APPLICATIONS

Reference is made to, and priority is claimed from, U.S. Ser. No. 61/323,503, filed as a provisional patent application on Apr. 13, 2010, entitled "MOBILE UNIT HAVING COLLAPSIBLE COLUMN", in the names of William C. Wendlandt et al. and commonly assigned.

FIELD OF THE INVENTION

The present invention relates generally to the field of radiography and in particular to portable radiographic imaging apparatus. More specifically, the invention relates to column height adjustment in a mobile radiography apparatus having a collapsible support column with an x-ray boom of adjustable height.

BACKGROUND OF THE INVENTION

Mobile x-ray apparatus are of particular value in intensive care unit (ICU) and other environments where timely acquisition of a radiographic image is important. Because it can be wheeled around the ICU or other area and brought directly to the patient's bedside, a mobile x-ray apparatus allows an attending physician or clinician to have recent information on the condition of a patient and helps to reduce the risks entailed in moving patients to stationary equipment in the radiological facility.

The perspective view of FIG. 1 shows an example of a conventional mobile x-ray apparatus that can be employed for computed radiography (CR) and/or digital radiography (DR). A mobile radiography unit 600 has a frame 620 that includes a display 610 for display of obtained images and related data and a control panel 612 with a keyboard that allows instruction entry for storing, transmitting, modifying, and printing of the obtained image.

For mobility, unit 600 has one or more wheels 615 and one or more handle grips 625, typically provided at waist-, arm-, or hand-level, that help to guide unit 600 to its intended location. A self-contained battery pack typically provides source power, eliminating the need for operation near a power outlet.

Mounted to frame 620 is a columnar support member 635 that supports an x-ray source 640, also termed an x-ray tube, tube head, or generator mounted on a boom apparatus 70, more simply termed a boom 70. In the embodiment shown, support member 635 has a vertical column 64 of fixed height. Boom 70 extends outward a variable distance from support member 635 and translates up and down column 64 to the desired height for obtaining the image. Boom 70 may extend outward by a fixed distance or may be extendible over a variable distance. Height settings for the x-ray source 640 can range from low height for imaging feet and lower extremities to shoulder height and above for imaging the upper body portions of patients in various positions. In other conventional embodiments, the support member for the x-ray source is not a fixed column, but is rather an articulated member that bends at a joint mechanism to allow movement of the x-ray source over a range of vertical and horizontal positions.

One concern that must be addressed in design of the support member relates to ease of positioning of the x-ray source mounted on its boom. For ease of operation under varying conditions, the technician should be able to easily position and orient the x-ray source without requiring both hands, without the need of additional tools, and without needing help from nearby personnel. This includes moving the x-ray source from its docked position used in transport to an imaging position. The mechanical problem of providing ease of positioning is complicated by the weight of the x-ray source and by its extension outward from the vertical axis, While the conventional mobile x-ray apparatus described as unit 600 provides portable imaging capability in a number of applications, however, there are drawbacks to existing designs that can make these devices difficult to deploy in some circumstances. One of the problems common to conventional designs is due, in part, to the relative mobility and range of motion of the mobile x-ray apparatus that is needed.

The side view of FIG. 2 shows a significant problem that occurs when transporting a mobile radiography system, shown as a mobile radiography unit 62 that uses a fixed vertical structure, column 64. Boom 70 that provides transport of x-ray source 68, normally extended outward from unit 62 when in its imaging position, is folded back toward a technician 66 for transport. This transport position helps to protect the x-ray source from damage or from causing an obstruction during movement. Column 64, however, obstructs the view of technician 66 when moving the unit from one place to another, so that objects that are near the front edge of unit 62 or directly in front of the unit cannot readily be seen. The technician is required to peer around the column during transport and can be more prone to colliding or bumping against other equipment or obstacles in the hospital ward or other location. The fixed vertical column 64 may also present difficulties when passing or moving alongside accessory equipment, furniture, or patient support equipment. With obstructed vision, the technician must move slowly, impacting productivity and response time. Accidents and mishaps are more likely.

One type of solution for alleviating the visibility and mobility problems described with reference to FIG. 2 is to provide a collapsible column 64, as described in commonly assigned U.S. Patent Application Ser. No. 61/323,503 filed Apr. 13, 2010 in the names of Wendlandt et al. Making column 64 collapsible, such as using a telescopic column design, not only allows improved visibility during movement of the mobile radiography unit 62, but also provides a more favorable weight distribution that is more compact and has a lowered center of gravity, facilitating movement of the unit by the technician from room to room.

While the collapsible column has advantages over fixed column height, however, a number of problems remain to be solved. One area of particular interest relates to boom movement for height adjustment. Because both the column height and boom height are adjustable, some amount of coordination is useful to help make it more natural to switch between various height positions, preferably so that the technician can concentrate attention on obtaining the best setup conditions for exposure without excessive concern for setting or adjusting column height relative to boom height.

Thus, there is a need for improvements in mobile x-ray apparatus design that allow ease of height adjustment of a collapsible column relative to the height of its boom transport mechanism.

SUMMARY OF THE INVENTION

An object of the present invention is to advance the art of mobile radiography. Another object of the present invention is to address the need for a mobile radiography unit that allows ease of movement of the boom assembly between vertical positions.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

From one aspect, the present invention can provide a mobile radiography apparatus comprising: a portable transport frame; a sectioned vertical column mounted on the frame and defining a vertical axis and comprising a base section having a first vertical position relative to the vertical axis and at least one movable section that is translatable to a variable vertical position along the vertical axis; a counterbalance apparatus coupled to the at least one movable section of the vertical column and comprising an actuator that is energizable to translate the at least one movable section along the vertical axis; a boom apparatus supporting an x-ray source and coupled to the at least one movable section for vertical displacement of the boom apparatus to a height position; and a height sensing element that provides a signal that is indicative of the height position of the boom apparatus.

From an alternate aspect, the present invention can provide a mobile radiography apparatus comprising a portable transport frame; a sectioned vertical column mounted on the frame and defining a vertical axis and comprising a base section having a fixed vertical position relative to the vertical axis and a movable section that is translatable to a variable vertical position along the vertical axis; a counterbalance apparatus coupled to the movable section of the vertical column and comprising a tension force element and an actuator that is energizable to translate the movable section along the vertical axis; a boom apparatus supporting an x-ray source and movably coupled to the movable section for vertical displacement of the boom apparatus to a height position within a range of height positions along the movable section; and one or more height sensing elements that provide one or more signals that are indicative of the height position of the boom apparatus on the movable section of the vertical column.

From an alternate aspect, the present invention can provide a method for setting up a portable radiographic unit for an exposure, comprising mounting a sectioned vertical column on a portable transport frame, wherein the column defines a vertical axis and comprises a base section having a first vertical position relative to the vertical axis and at least one movable section that is vertically translatable to extend the vertical column along the vertical axis; coupling a counterbalance apparatus to the at least one movable section of the vertical column, the counterbalance apparatus comprising an actuator that is energizable to translate the at least one movable section along the vertical axis; coupling a boom apparatus supporting an x-ray source to the at least one movable section for vertical displacement of the boom apparatus to a height position; and responding to an operator instruction to adjust the height of the boom apparatus for the exposure by translating the at least one movable section along the vertical axis.

From an alternate aspect, the present invention can provide a method for setting up a portable radiographic unit for an exposure, comprising providing a sectioned vertical column mounted on a portable transport frame, wherein the column defines a vertical axis and comprises a base section having a fixed vertical position relative to the vertical axis and a movable section that is translatable to a variable vertical position along the vertical axis; coupling a counterbalance apparatus to the movable section of the vertical column, the counterbalance apparatus comprising at least an actuator that is energizable to translate the movable section along the vertical axis; coupling a boom apparatus supporting an x-ray source to the movable section for vertical displacement of the boom apparatus to a height position, wherein the boom apparatus is movably displaceable vertically over a range that extends along at least a portion of the movable section; and adjusting the height of the vertical column for the exposure in response to upward or downward urging of the boom apparatus by an operator.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 13 is a perspective view showing the boom transport on the upper section of the collapsible column, with the transport in a lower position.

FIG. 14A is a top view showing the carriage mechanism of the boom transport in one embodiment.

FIG. 14B is a side view showing the carriage mechanism of the boom transport in the FIG. 24A embodiment.

FIGS. 16A and 16B show schematically the use of a counterweight that is elongated, according to one embodiment of the present invention, with the boom apparatus in raised and lowered positions, respectively.

FIGS. 17A, 17B, and 17C are schematic views that show a number of possible combinations for achieving the same height for the boom apparatus using an embodiment with an elongated counterweight.

FIG. 19A is a block diagram showing the column in collapsed condition with the boom apparatus near the bottom of its travel path.

FIG. 19B is a block diagram showing the column extended with the boom apparatus traveling upward along its travel path.

FIG. 19C is a block diagram showing the column in fully extended condition with the boom apparatus near top bottom of its travel path.

FIG. 19D is a block diagram showing the column extended with the boom apparatus traveling downward along its travel path.

DETAILED DESCRIPTION OF THE INVENTION

Figure 1:
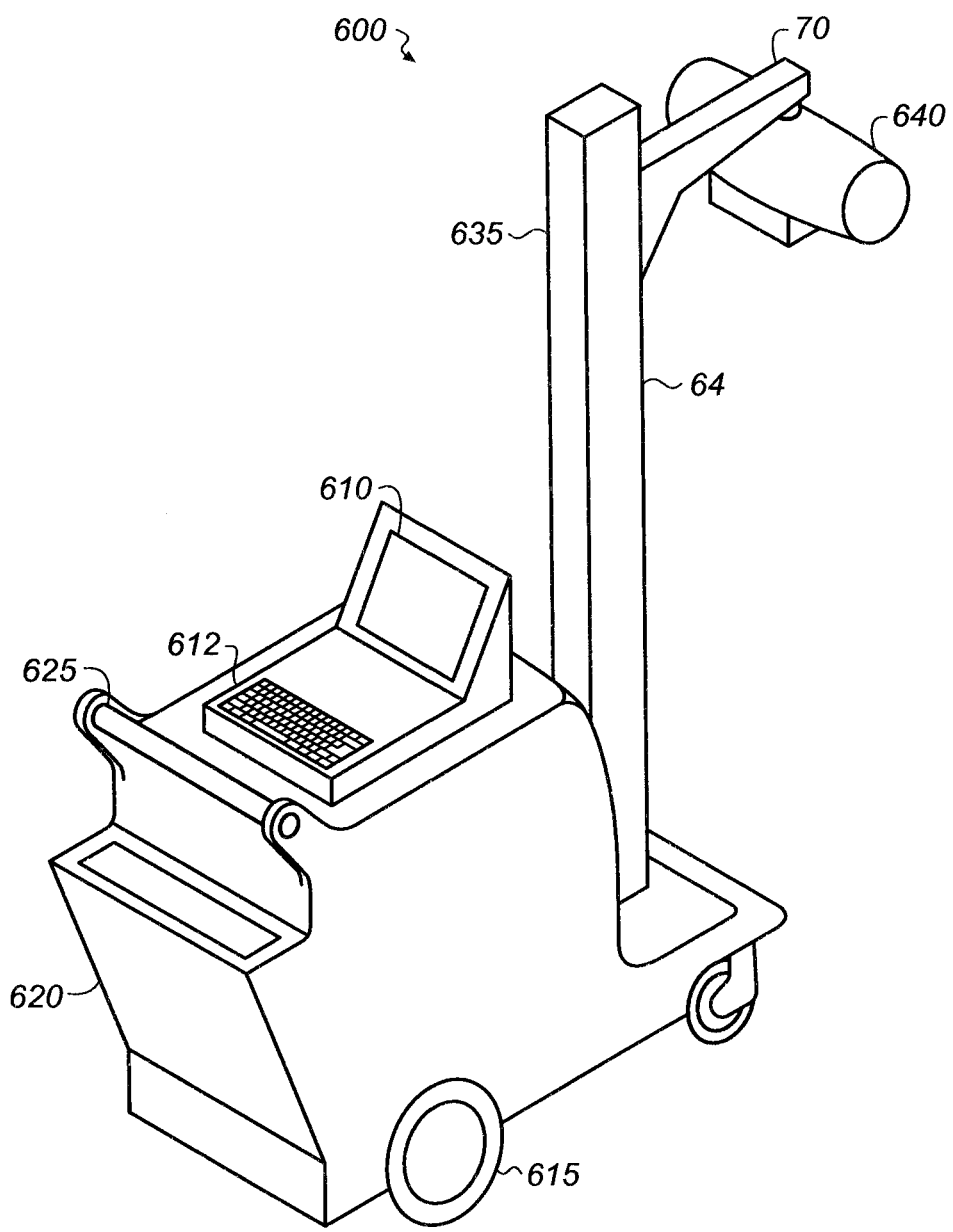
FIG. 1 shows a perspective view of a conventional mobile radiography unit using a fixed length vertical column for positioning the x-ray source.

The following is a detailed description of the preferred embodiments of the invention, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

Figure 2:
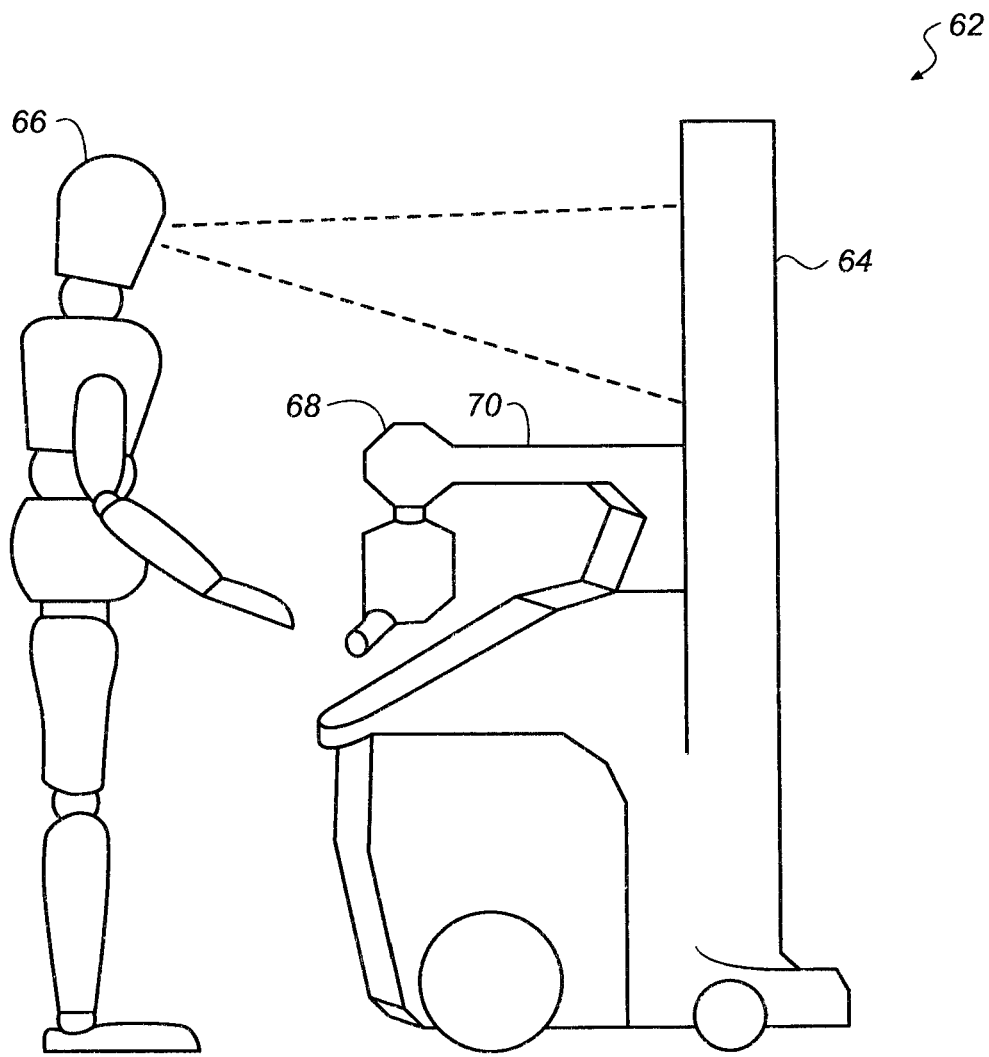
FIG. 2 shows a side view of a conventional mobile radiography unit with a fixed vertical column for positioning the x-ray source.

Apparatus and methods of the present invention address the need for a radiography unit that can be readily wheeled from one place to another within a treatment facility, without the physical or visual obstruction that is common to many types of conventional mobile radiography equipment that use a vertical column. As noted previously, the x-ray source of such a system must allow elevation over a wide vertical range of motion, from heights near or above shoulder level for adults to very low elevations near the ankle or foot. One way to achieve this range of movement is the use of a jointed support member, as described previously. A somewhat simpler mechanical design is the use of a stationary vertical column as was shown in FIGS. 1 and 2, with the x-ray source mounted on a boom that extends outward horizontally from the column and travels vertically up and down the column. Two degrees of freedom are needed for boom 70 movement relative to the vertical column: translation along the vertical direction, that is, along the vertical axis, and rotation about the vertical axis. Boom 70 typically also extends to a variable horizontal length in a direction relative to the vertical axis, although it should be noted that a boom of fixed length could be used in a mobile radiography apparatus of the present invention.

Figure 3:
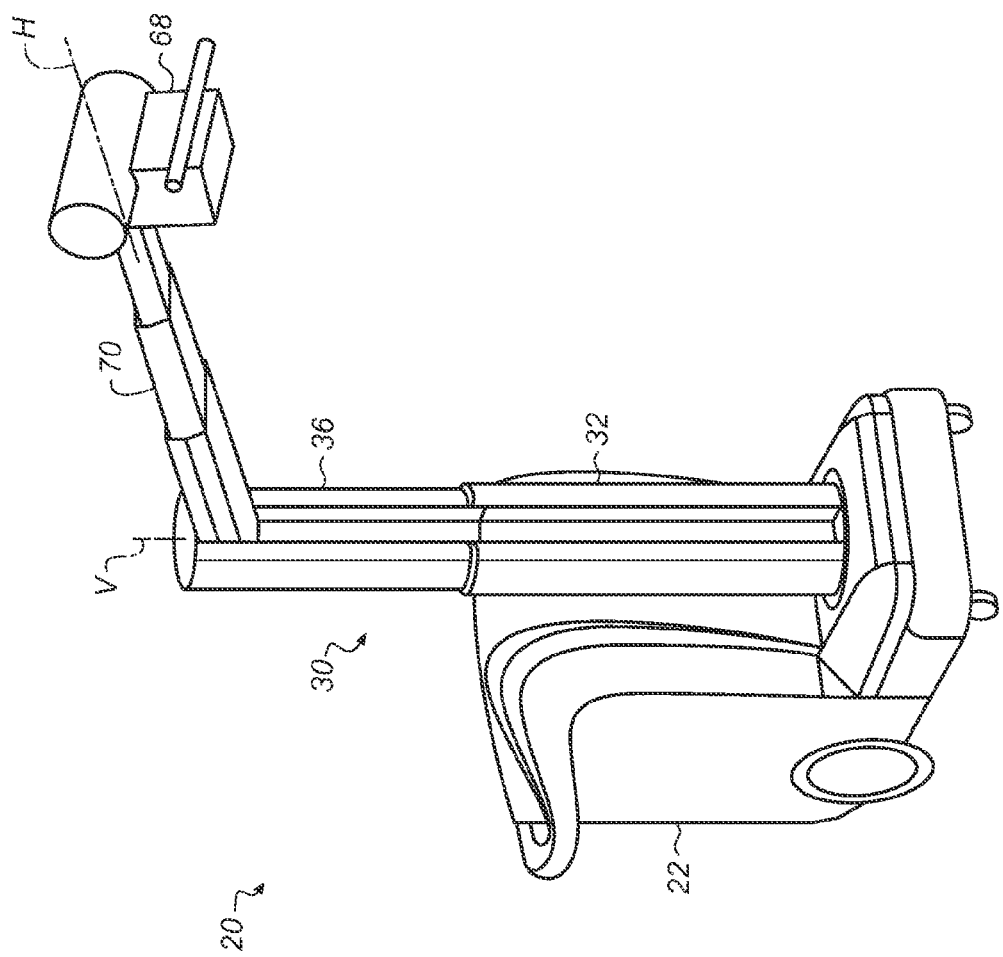
FIG. 3 shows a perspective view of a mobile radiography unit with a sectioned vertical column according to one embodiment of the present invention.
Figure 4:
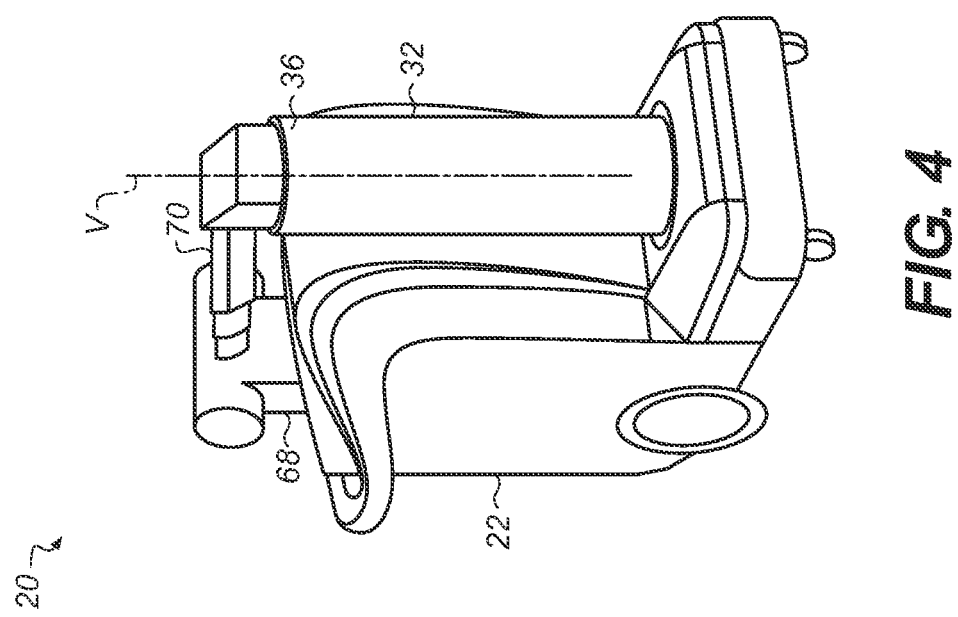
FIG. 4 shows a perspective view of a mobile radiography unit with a sectioned vertical column configured for travel.

The perspective view of FIG. 3 shows a mobile radiography unit 20 that has boom 70 coupled to a sectioned vertical column 30 according to one embodiment. FIG. 3 shows unit 20 with x-ray source 68 in position for imaging, extended outward and supported on boom 70, along a horizontal axis H that is perpendicular to the vertical axis V. FIG. 4 shows unit 20 in an alternate arrangement, configured for travel, with sectioned vertical column 30 collapsed and with x-ray source 68 nestled against a top surface of the unit. The side view of FIG. 5 shows unit 20 configured for travel and shows how, using the collapsed column, technician visibility is improved over the conventional fixed vertical column arrangement shown previously in FIGS. 1 and 2.

Figure 6:
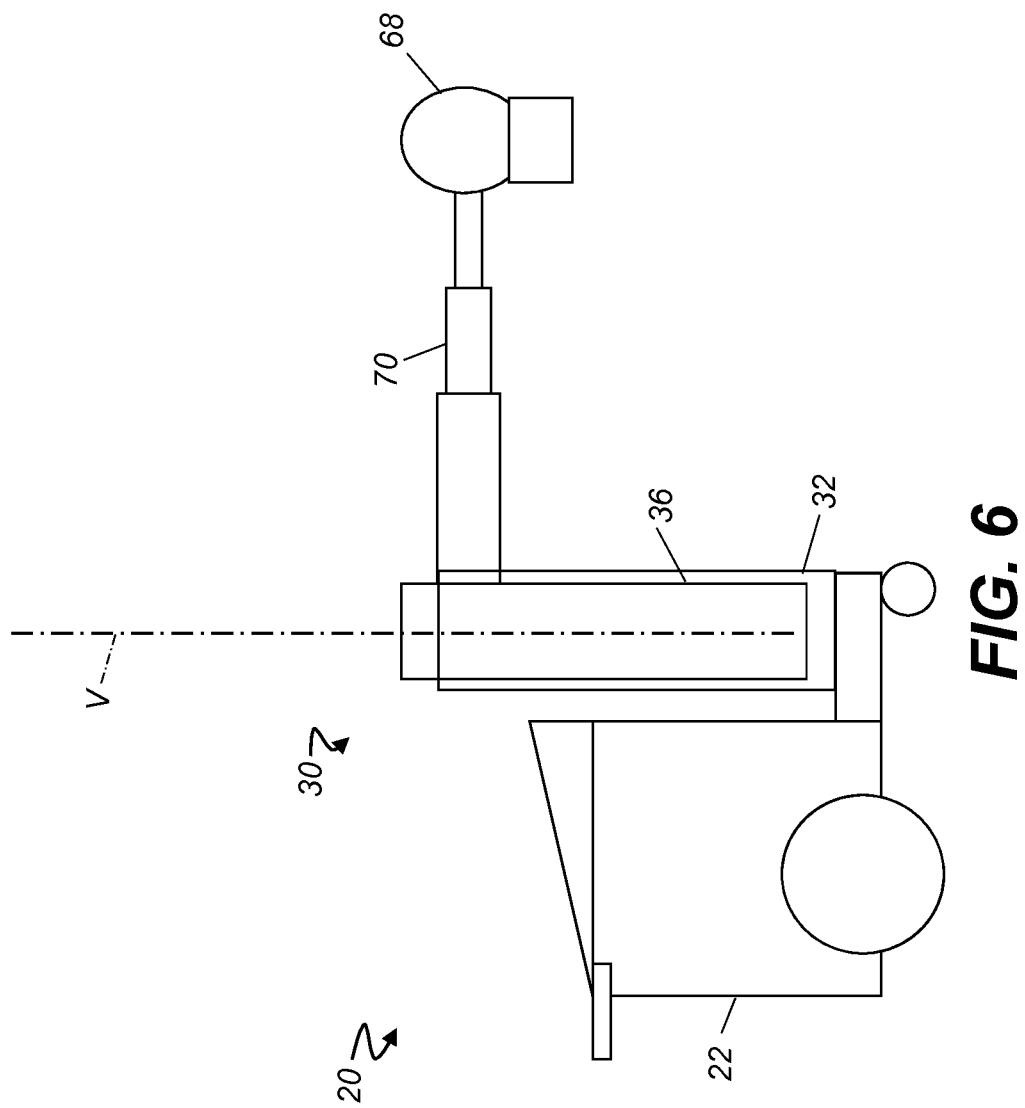
FIG. 6 is a side view showing a mobile radiography unit having a sectioned vertical column in collapsed position.
Figure 7:
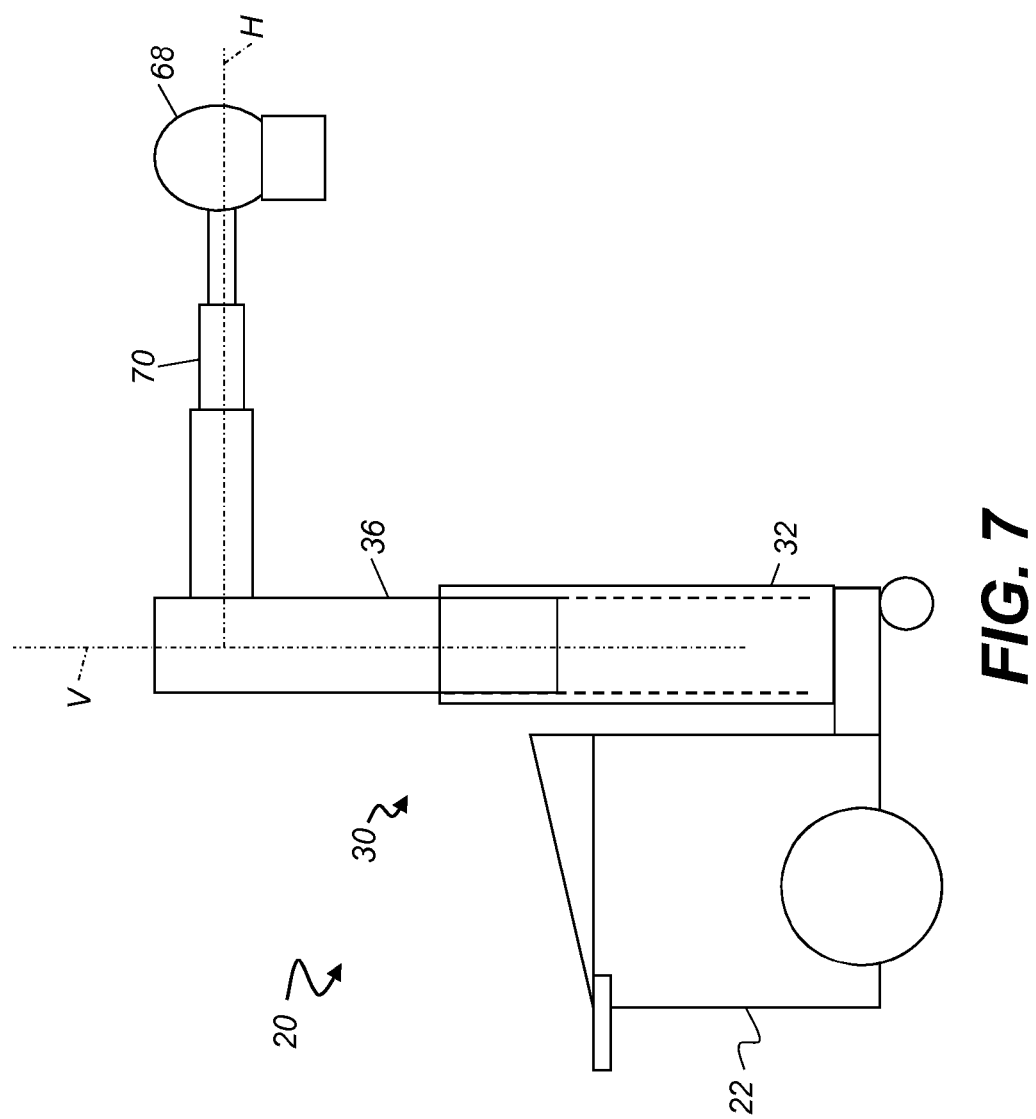
FIG. 7 is a side view showing a mobile radiography unit having a sectioned vertical column that is fully extended for patient imaging.
Figure 8:
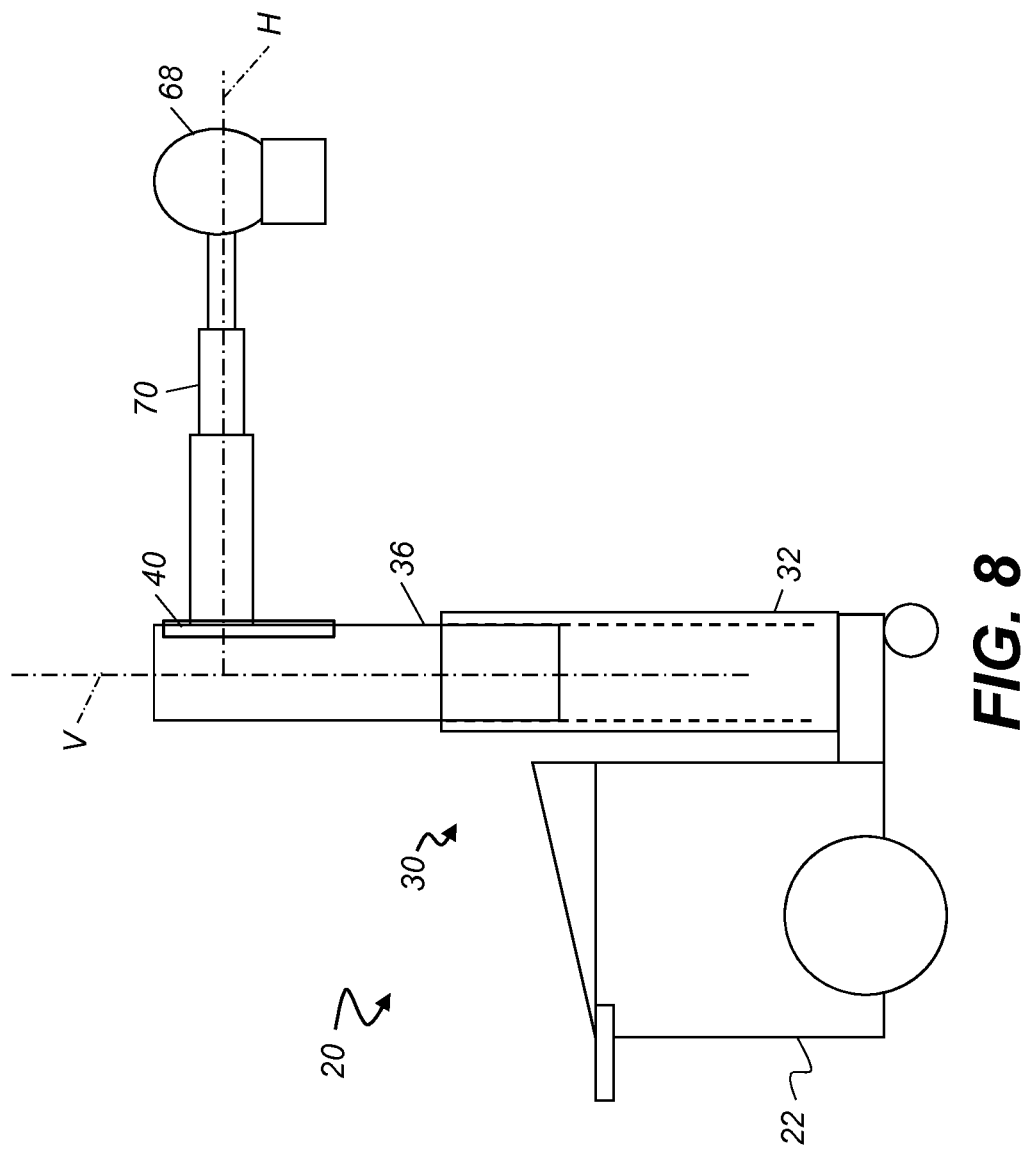
FIG. 8 is a side view showing a mobile radiography unit having a sectioned vertical column that is fully extended for patient imaging with a boom transport mechanism for the x-ray source.

In each of the embodiments shown in FIGS. 6-8, mobile radiography unit 20 has a wheeled transport frame 22 and has display and control panel components needed for operation, as was described previously with reference to FIG. 1. Sectioned vertical column 30, mounted on frame 22, defines a vertical axis V and has a base section 32 that seats against frame 22 and has a first vertical position relative to axis V, a fixed vertical position in one embodiment. One or more movable sections 36 are translatable to extend along the vertical axis V, so that boom 70 can be set to a suitable height over a range of possible height settings. In each embodiment, x-ray source 68 can be set to variable vertical and horizontal positions as well as to a range of angular positions about the vertical axis V.

In the embodiment shown in FIGS. 6 through 19D, sectioned vertical column 30 has a single movable section 36. Section 36 is movable in telescoping fashion with respect to stationary base section 32. Boom 70 extends outward from sectioned vertical column 30 and can be rotated at least over some angular range into position about vertical axis V. Rotation about axis V can be achieved in a number of ways. In the embodiments shown in FIGS. 6 through 19D, sectioned vertical column 30 itself rotates in relation to its transport frame 22. In an alternate embodiment, only the outermost movable section 36, with its attached boom 70, rotates. In each of these embodiments, both rotation about vertical axis V and vertical displacement along the vertical axis can be performed simultaneously.

Figure 5:
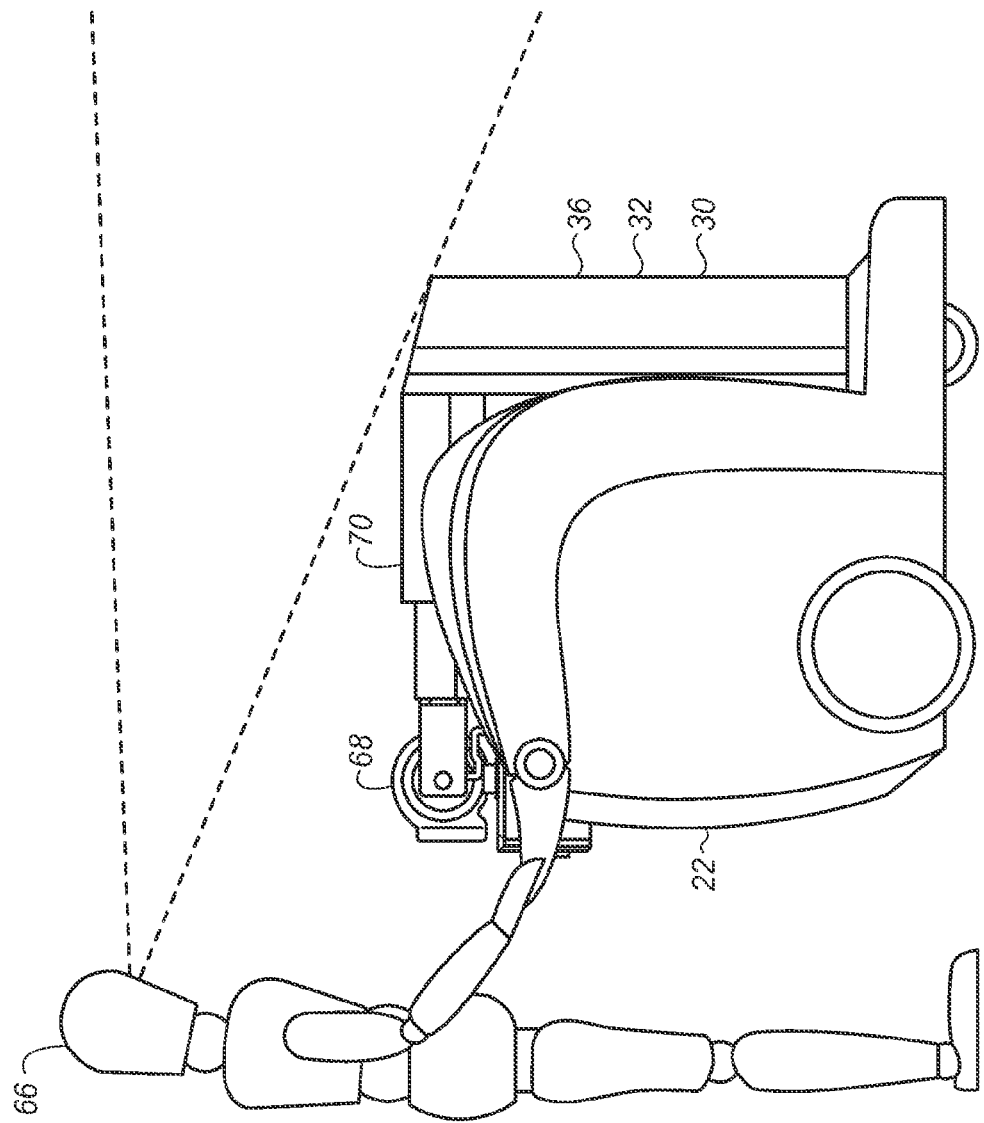
FIG. 5 shows a side view of a mobile radiography unit with a sectioned vertical column according to one embodiment of the present invention.

In the travel configuration of FIG. 5, sectioned vertical column 30 is collapsed and boom 70 is rotated inward in order to seat x-ray source 68 in a stable, docked position for movement, such as for wheeling from one patient area to another. FIG. 6 shows initial elevation of sectioned vertical column 30 upward from its travel position and rotated, readying the unit for deployment. FIG. 7 shows vertical column 30 fully extended, with boom 70 facing outward and with movable section 36 at its extreme end of travel, with x-ray boom 70 extended orthogonally outward from sectioned vertical column 30 along horizontal axis H, ready for imaging in this position.

It is beneficial to allow the fullest possible range of vertical heights for the x-ray source in a portable system, from above shoulder height of the imaging technician to relatively low elevations, such as might be beneficial for imaging the foot or ankle of a patient. It can be appreciated that this desired height range presents a problem for telescoped column designs. When a telescoped column is fully collapsed, as shown in FIG. 6, boom 70, when attached in fixed position along movable column 36, can no longer be moved downward. This movement limitation can make the telescoping arrangement less desirable for portable radiography systems.

Embodiments of the present invention address this difficulty by using a boom transport mechanism that cooperates mechanically with a telescoping, sectioned vertical column to allow displacement of the x-ray boom over a wide range of height settings. Advantageously, the operator can easily adjust x-ray boom height, with the weight of column and boom components mechanically balanced so that a substantially uniform amount of effort is needed for height adjustment to any level within the height range.

Figure 9:
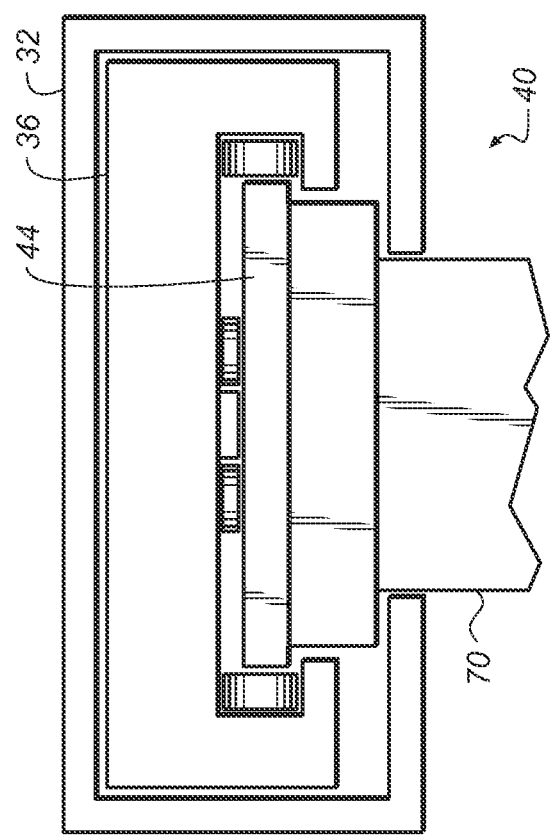
FIG. 9 is a top view cross-section of the sectioned vertical column showing the movable section within the fixed outer base section.

The side views of FIG. 8 and following show an embodiment of mobile radiography unit 20 in which a boom transport mechanism 40 is mounted on movable section 36 and is actuable to provide the added vertical range needed for imaging with source 68 at a low elevation below the range that is typically feasible with sectioned vertical column 30 fully collapsed when using the embodiment shown in FIG. 6. Boom transport mechanism 40 allows a second mode of vertical displacement for boom 70, so that not only is boom 70 mounted on a vertically collapsible column, but its vertical travel is further permitted for a distance along the length of the movable section. FIG. 9 shows a top view cross-section of sectioned vertical column 30 in the FIG. 8 embodiment, showing movable section 36, with a carriage 44 as part of boom transport mechanism 40, supporting boom apparatus 70 within fixed outer base section 32.

Figure 10:
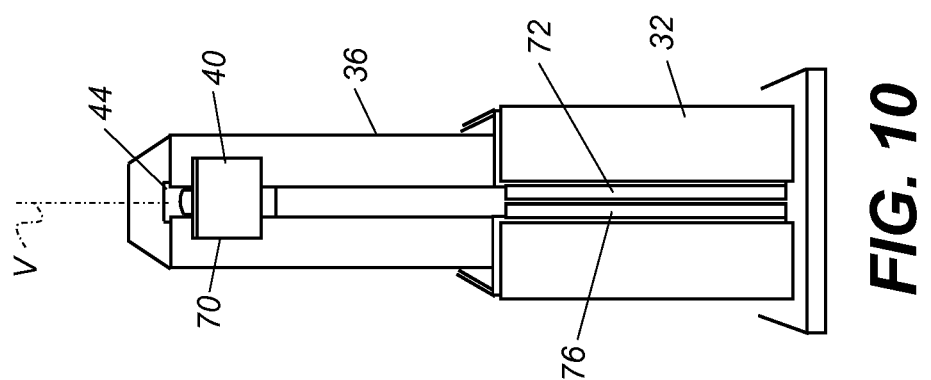
FIG. 10 is a perspective view of the sectioned vertical column of FIG. 8, with boom portions removed for visibility.

FIG. 10 is a perspective view of the sectioned vertical column of FIG. 8, with boom portions removed for better visibility. When movable section 36 travels inside base section 32, a vertical opening 72 is provided in base section 32. Opening 72 allows boom apparatus 70 to travel along the length of base section 32 when in the collapsed column configuration. In one embodiment, a sleeve 76, formed from a resilient material such as rubber or plastic or using brushes or other suitable material, provides a protective covering over opening 72 that allows boom apparatus 70 travel along the opening.

An important design consideration for usability of mobile radiography unit 20 is the ease of movement that is needed for positioning x-ray source 68 in the proper position relative to the patient and to the x-ray detector panel. This is a complex mechanical problem due, in part, to the weight of the x-ray tube and its collimator, which can exceed 100 pounds in some systems. The operator should be able to readily move x-ray source 68 to the needed vertical and horizontal position without undue exertion. In addition, the amount of effort needed to adjust the elevation of x-ray source 68 should be balanced over its full range of vertical displacement, so that substantially no additional effort is needed to adjust the height from any one level to any other.

Figure 11:
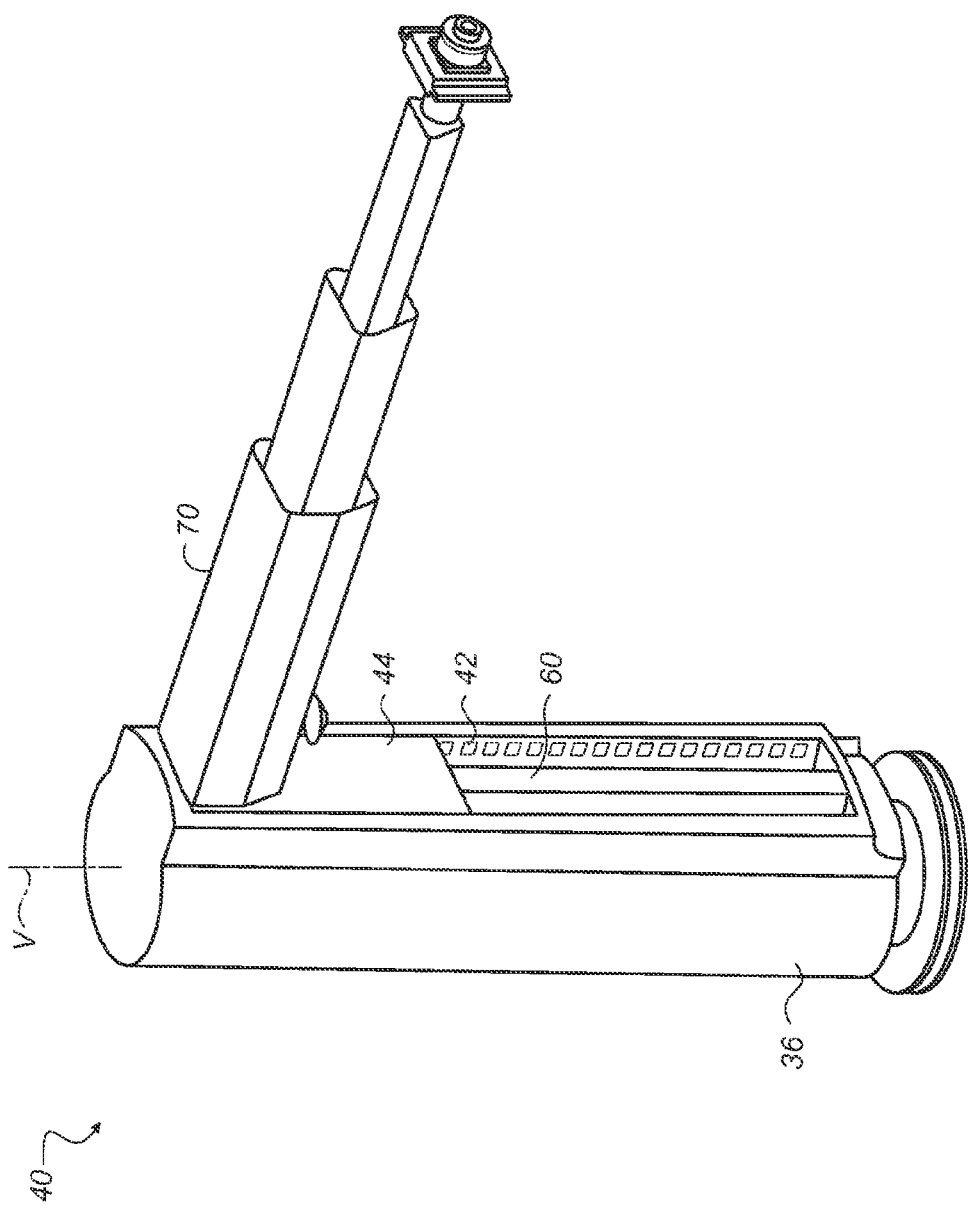
FIG. 11 is a perspective view showing the boom transport on the upper section of the collapsible column, with the transport in an upper position.
Figure 12:
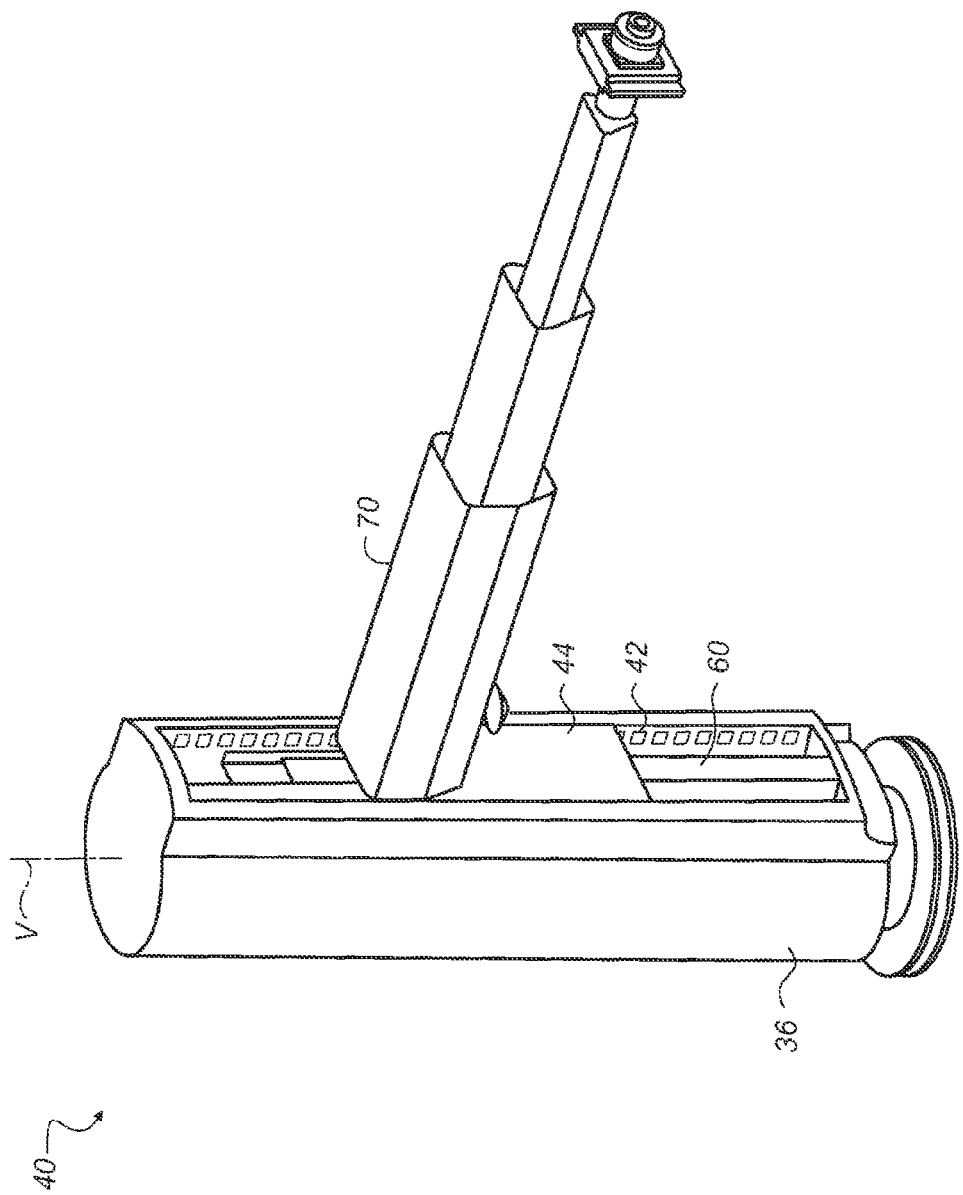
FIG. 12 is a perspective view showing the boom transport on the upper section of the collapsible column, with the transport in a middle position.

The perspective views of FIGS. 11, 12, and 13 show boom transport mechanism 40 and carriage mechanism 44 in different vertical positions along upper movable section 36. In these figures, boom transport mechanism 40 is coupled to section 36 by wheeled carriage mechanism 44 that is movable within a track 42.

Boom transport mechanism 40, shown in schematic detail in top and side views of FIGS. 14A and 14B, respectively, has a series of wheels 54 that rotate within a track 42 to provide vertical displacement. Four wheels are used for this function in the embodiment shown in FIGS. 14A and 14B. Two additional pairs of wheels 58 rotate in an orthogonal direction against a centering block 60 in order to constrain unwanted side-to-side movement of boom 70 relative to the vertical axis. It can be appreciated that alternative embodiments can be used for boom transport mechanism movement, including the use of one or more linear bearings, sliders, for example.

Figure 15B:
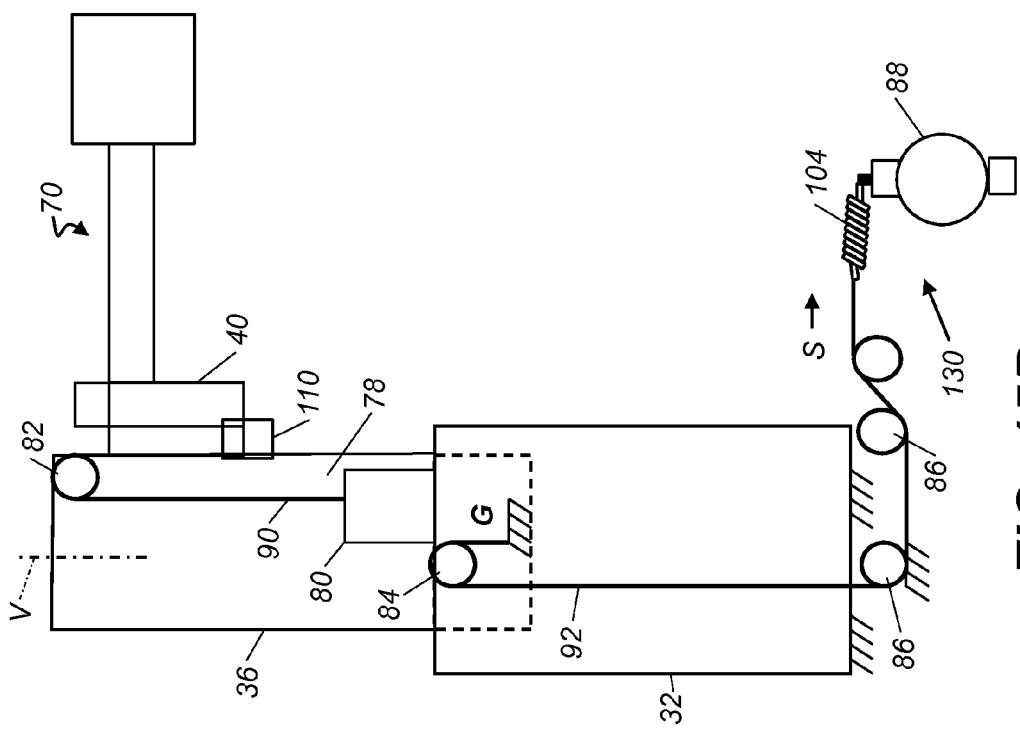
FIGS. 15A and 15B show schematically how a counterweight is deployed in order to provide a lifting force for a boom apparatus in an embodiment of the present invention that uses a sectioned vertical column.
Figure 15A:
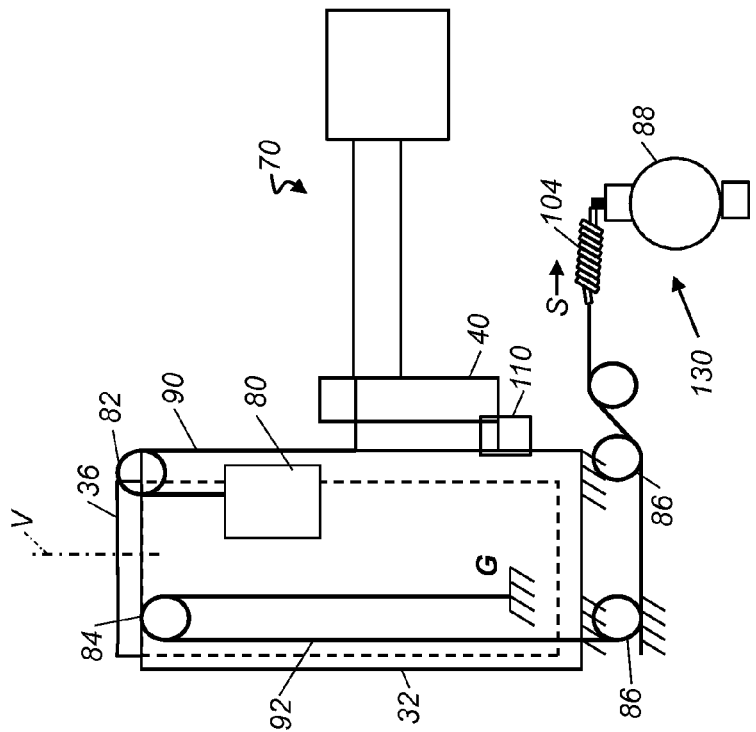

FIGS. 15A and 15B show schematically how a counterweight 80 is deployed in order to provide a lifting force for boom apparatus 70 in an embodiment of the present invention that uses a sectioned vertical column. FIG. 15A shows boom apparatus 70 at a low elevation, with the section column collapsed, such as might be used for imaging a patient's foot or lower leg, for example. FIG. 15B shows the column in an extended position, with movable section 36 extended from base section 32 and boom apparatus 70 raised toward its maximum height. Counterweight 80 is operatively coupled to boom apparatus 70 by means of a pulley 82 and a cable 90. In cooperation with boom apparatus 70 movement, counterweight 80 is vertically displaced along a shaft 78, a cavity that extends within the column, in the direction of the vertical axis V.

In the embodiment shown in FIGS. 15A and 15B, components of a counterbalance apparatus 130 are shown. A counterbalance force S is provided by a tension force element 104, such as a tension spring, for example. A motor 88 or other actuator provides additional counterbalance force when needed to drive movable section 36 toward a desired vertical position. An optional height sensing element 110 is energizable to provide a signal that is indicative of either or both the column height and/or the vertical position of boom apparatus 70 relative to movable section 36. This signal is used to actuate motor 88 when needed, as described in more detail subsequently. To provide a lifting force, a cable 92 is routed around a pulley 84 and through wheels 86 to tension force element 104 and motor 88 or other actuator. A mechanical ground to movable column 36 is shown at G.

Counterweight 80 travels within shaft 78 that is internal to the sectioned column, with the column dimensionally sized for portability. This sets some constraints on the overall width dimension (that is, dimensions orthogonal to the vertical axis V) that can be allowed for this heavy counterweight 80 component, whose weight, and thus the counterweight force available, depends both on its volume and on the mass of its component material. Lead is conventionally used for counterweights, but other materials that are considered less hazardous are preferred and can be used if additional volume is provided. In addition to volume constraints, it is preferable that the operator be shielded from possible inadvertent contact against moving parts such as internal pulleys, cables, and related moving components that relate to boom or column movement.

Figure 16D:
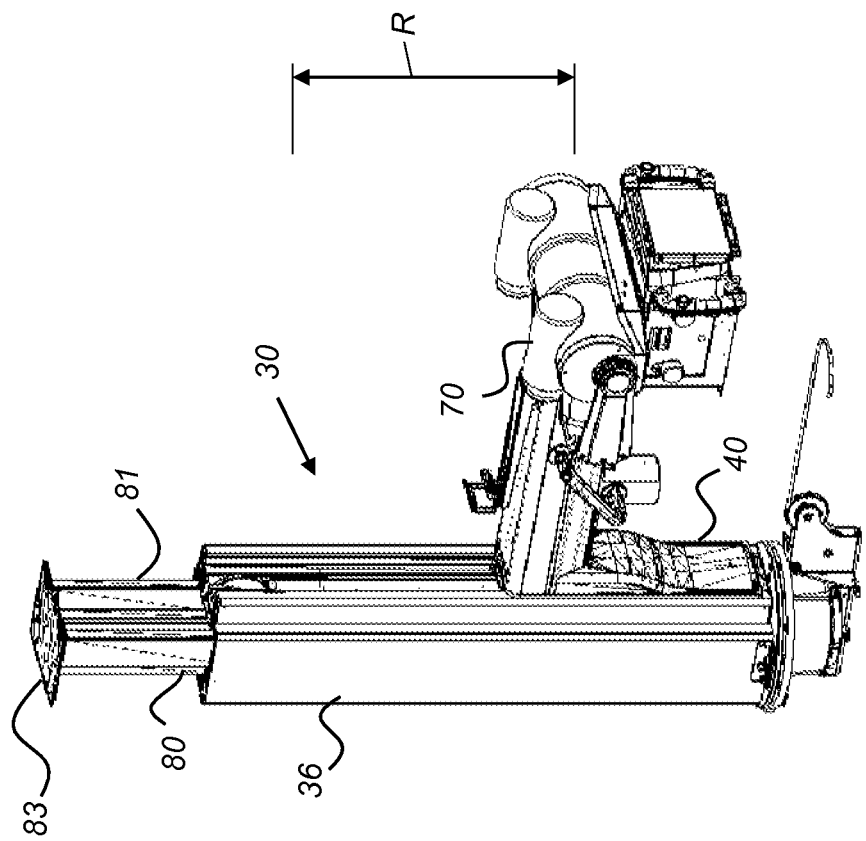
FIGS. 16C and 16D are perspective views that show boom apparatus in the raised and lowered position and show the counterweight element extending upwards when the boom is lowered.
Figure 16C:
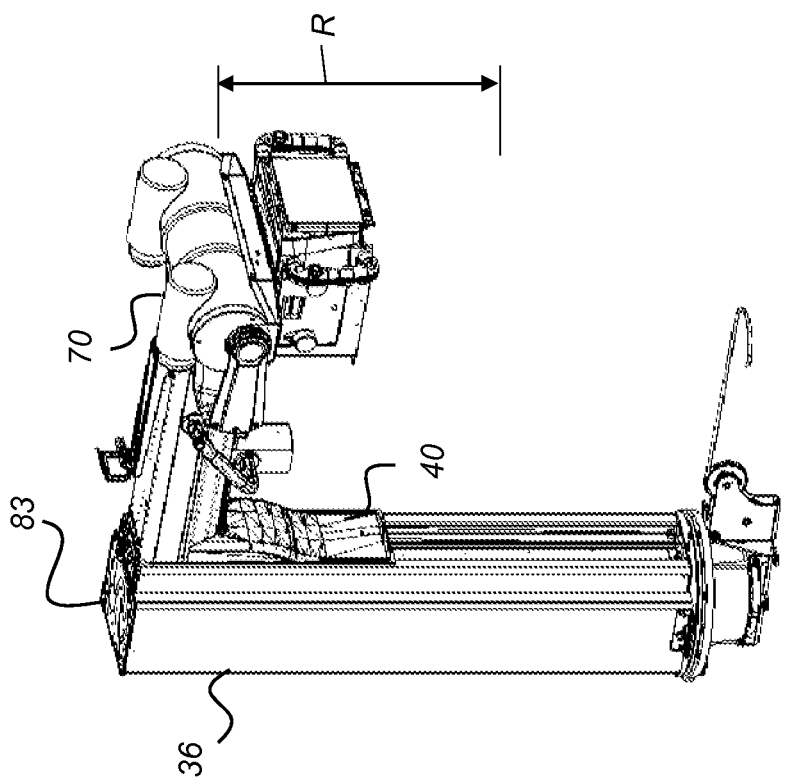

As shown schematically in FIGS. 16A and 16B, and in perspective views in corresponding FIGS. 16C and 16D, embodiments of the present invention address the problem of limited width dimension by extending the length of counterweight 80 in the vertical direction. An extended section 81 adds volume to counterweight 80 in an upward vertical direction. FIGS. 16A-D also show a range R of boom 70 displacement relative to column section 36. Range R depends on a number of factors, including the height of movable section 36 and the arrangement of boom transport mechanism 40 components. In one embodiment, for example, range R is between 24 and 30 inches.

FIGS. 16A and 16B show vertical column 30 in a collapsed configuration. As shown in FIGS. 16B and 16D, with boom 70 lowered, extended section 81 of counterweight 80 can protrude or extend above shaft 78, whose top edge is defined by a top edge 79 of vertical column 38. An optional cap 83 is provided to cover shaft 78 in the embodiment of FIGS. 16C and 16D. FIG. 16B shows a shaft height H2, in an embodiment in which shaft 78 extends fully through stationary column 32. In an alternate embodiment, shaft 78 extends only partway through column 32. In a multi-column section embodiment, the top of shaft 78 is defined by the top edge 79 of the uppermost movable column.

FIGS. 17A, 17B, and 17C show sectioned vertical column 30 with base section 32 and movable section 36. As these figures show, the combination of variable column height and variable counterweight 80 position allows a number of possible combinations for achieving the same height H1 for boom apparatus 70. In FIG. 17A, for example, movable section 36 is extended upwards and extended section 81 of counterweight 80 protrudes from the top of shaft 78 by a distance D1 when height H1 is achieved. Here, boom 70 is displaced to near the bottom of displacement range R. In FIG. 17B, the same height H1 is reached with movable section 36 somewhat less extended; here, boom 70 is displaced near the middle of its displacement range R and extended section 81 of counterweight 80 protrudes from the top of shaft 78 by a lesser distance D2. In FIG. 17C, the column is collapsed and, with boom 70 at the position shown relative to movable column 36, near the top of its displacement range R, counterweight 80 is wholly enclosed within shaft 78, with no portion protruding above top edge 79. As can be seen from this example, there can be any number of possible arrangements of column and counterweight 80 components used for achieving intermediate heights of boom apparatus 70 with sectioned vertical column 30. An optional brake 52 is also provided that, when actuated, constrains or prevents vertical movement of movable section 36.

With respect to FIGS. 15A through 17C, it can be appreciated that other arrangements of component weights and pulley configurations are possible, as well as mechanical configurations using counterweights or various types of electromechanical or hydraulic actuators, for example. As shown in the examples given above, vertical column 30 can have one or more movable sections to allow variable height. Various types of mechanical brake configurations are also possible and may be provided for helping to stabilize vertical movement of column sections or of the boom apparatus 70 itself.

Adjusting Column Height

As has been described with reference to FIGS. 15A through 17C, proper adjustment of the column 30 height controls the range of vertical movement that is allowed for adjustment of the boom apparatus 70 height. There are a number of considerations for setting the column height, including the type of image to be obtained; conditions such as the height of the patient's bed or other support, and the angle of the receiver relative to horizontal.

Embodiments of the present invention use different approaches for setting the height of column 30, for example:

(i) Direct operator control. Using this approach, the operator initiates an instruction to alter the height of column 30. This instruction is entered at control panel 612 (FIG. 1) or at a separate switch or control dedicated to this purpose. Using this method, the operator can enter or step to a set height, or hold down a keyboard key or switch until a desired height setting is achieved.

(ii) Automatic height setting according to view type. Using this approach, the operator setup includes specifying the view type of the image, such as an AP chest x-ray, for example. According to one embodiment of the present invention, setting a view type also selects an associated default column height value, so that the radiography system automatically adjusts the column height according to an operator instruction, as part of operator setup for the exposure. This information is entered at control panel 612 (FIG. 1) or using a separate switch or control dedicated to this purpose. Alternately, the operator can enter additional information, including the height of the patient's bed or supporting platform and the angle of the receiver relative to true horizontal or vertical or relative to the collimator on the tube head.

(iii) Assisted operator positioning. Using this approach, the operator manually lifts or lowers the boom to the desired height setting and the column height adjusts accordingly. Using this method allows the operator to ignore the column height setting and to concentrate only on moving the boom and tube head into the correct position. Unlike approaches (i) and (ii), assisted operator positioning requires system interaction with operator movement. The operator instruction that controls the column height setting is thus entered by the operator in urging boom 70 upward or downward and can be detected, for example, by a signal from height sensing element 110. While not a requirement, it is advantageous to provide column height adjustment that is automated to provide smooth, continuous movement of the boom, so that the operator need not: exert extra effort when urging boom 70 upward or downward over different parts of the boom movement range.

Figure 18:
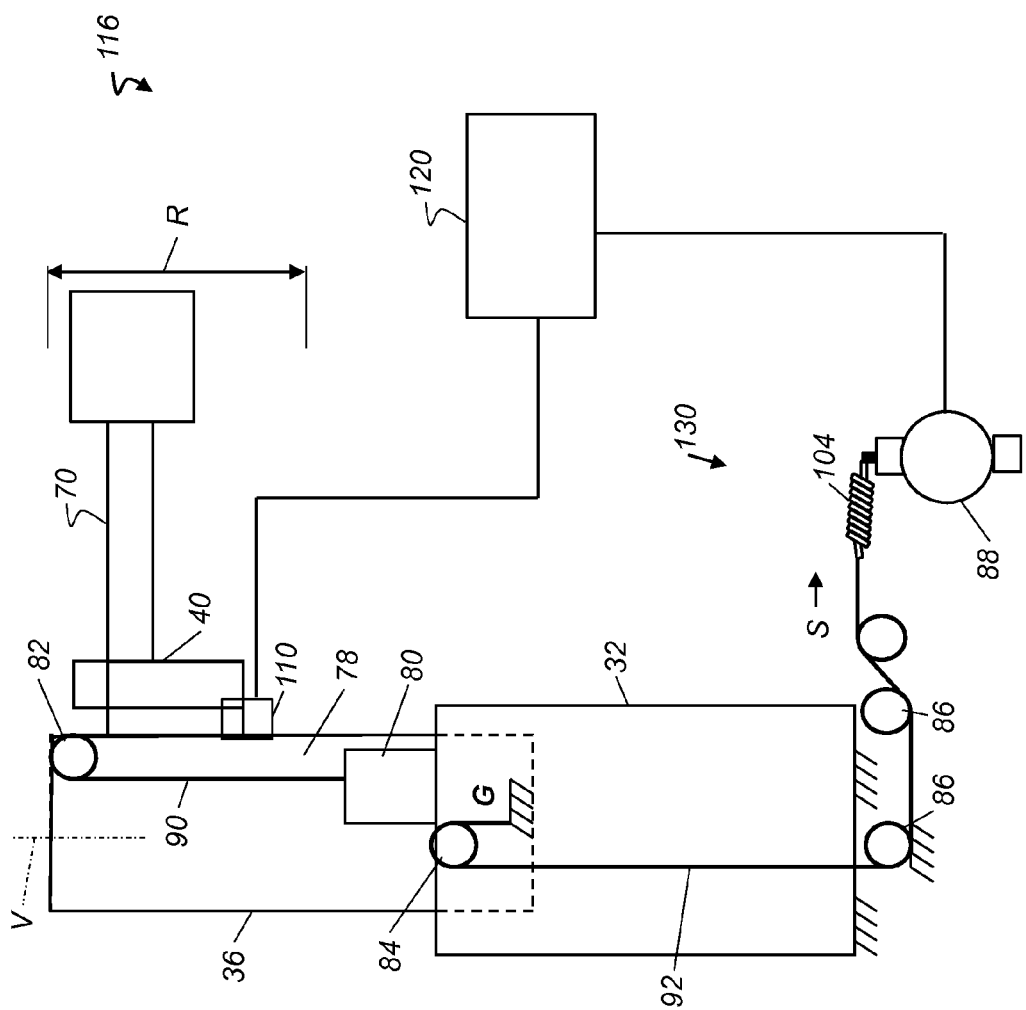
FIG. 18 is a block diagram that shows components of a column height adjustment apparatus according to an embodiment of the present invention.

The schematic block diagram of FIG. 18 shows a column height adjustment apparatus 116 that supports any of approaches (i), (ii), and (iii) listed above in an embodiment of the present invention. A control logic processor 120, which may be a dedicated processor, programmable logic array, or microprocessor, or may be the on-board computer provided for other functions of mobile radiography unit 20, is in signal communication with one or more height sensing elements 110 and with motor 88 or other actuator. Upon receipt of a signal indicating the need for column height adjustment, control logic processor 120 actuates motor 88 to change column height using the system of pulleys 84 and 86, cable 92, and tension force element 104. Where the signal is from direct operator control, as in (i) above, or according to view type for the exposure, as in (ii) above, the signal is obtained from control panel 612, the on-board control logic computer or processor, or other switch.

Column height adjustment for assisted operator positioning, as in (iii) above, is more complex because this requires coordination of column height with boom 70 position. This approach effectively uses boom 70 as the height control used by the operator. As has been noted previously, a goal for ergonomic column movement is to track boom displacement, so that boom 70 is at the extreme ends of displacement range R only when column 30 is either fully extended or fully collapsed. Otherwise, boom 70 moves freely within its displacement range R and the operator can ignore the column 30 height setting. This requires sensing the relative position of boom 70 to movable section 36 and compensating accordingly for boom 70 movement by adjusting column 30 height as a type of "background" operation, without requiring separate operator attention or instructions.

The block diagram of FIGS. 19A and 19B show how counterbalance apparatus 130 supports extension of sectioned vertical column 30 according to one embodiment. FIG. 19A shows the lowest height elevation for boom apparatus 70, at the extreme bottom of its displacement range R and with column 30 in its fully collapsed condition. As the operator lifts upward on boom 70, counterbalance apparatus 130 cooperates by providing corresponding extension of column 30. To allow smooth movement of boom 70, control logic processor 120 (FIG. 18) actuates counterbalance apparatus 130 to extend column 30 so that it leads the upward movement of boom 70, acting to effectively center displacement range R with respect to the current boom 70 position. It is not necessary to precisely reposition range R so that boom 70 is at or near the exact center of range R when moved to a particular height. Some lag or lead distance from exact centering may be appropriate for smooth movement, so that boom 70 does not reach its extreme ends of travel within range R other than when column 30 is at either its maximum extended height or at its minimum collapsed height.

A similar approach to motion control is used for downward movement of boom 70, with slight modification according to an embodiment of the present invention. By way of illustration, FIG. 19C shows boom 70 at its extreme height elevation, at the top of its displacement range R and with column 30 fully extended. As the operator lowers boom 70, control logic processor 120 (FIG. 18) senses this movement and compensates by lowering column 30, again with the goal of effectively centering displacement range R with respect to boom 70 position. Because boom 70 positions the x-ray tube above the patient, however, movement in the downward direction is slowed when compared with movement in the upward direction as was shown in FIG. 19B. Brake 52 may also be actuated for downward movement beyond a certain height or where movement speed, as indicated by height sensing element(s) 110 or other sensor element, exceeds a threshold value.

In the movement sequence described with reference to FIGS. 19A through 19D, motion control logic tracks the relative position of boom 70 in an interactive manner and is able to compensate for height change as well as for the rate of change. To do this requires that control logic processor 120 obtain and respond to updated information on boom 70 position and on column 30 height. In addition, the speed of translation of movable section 36 may change depending on how close boom apparatus 70 height is to the upper and lower boundaries of displacement range R. Control solutions for adapting both to changes in relative position and to varying rates of change in position, and for providing smooth motion in performing this compensation, are well known to those skilled in the motion control arts.

There are numerous ways to sense boom 70 displacement within its range R as well as column 30 height, using continuous or discrete sensors of various types, as is well known to those skilled in the motion control arts. In one embodiment, the sensor used as height sensing element 110 is a linear detection element, such as a linear encoder, that generates a signal that is indicative of boom 70 height with respect to column 30 or within displacement range R. This signal continually updates position information for control logic processor 120. Column 30 height is determined by motor driver logic, according to one embodiment. In an alternate embodiment, multiple sensor elements are used as height sensing elements 110, such as to indicate boom apparatus 70 position near each end of travel within range R. Discrete sensors for height sensing element 110 can alternately be limit switches or other switch elements positioned at various set-points for both boom 70 travel and column 30 height. A rotary encoder could alternately be used as height sensing element 110.

According to embodiments of the application, a sectioned vertical column of a mobile radiography apparatus can include a base section positioned at a first vertical position, at least a first movable section that is translatable to a variable vertical position, and at least one additional (e.g., intermediate) section translatable to a variable vertical position where these exemplary sections can be translatable to vary the height of the sectioned vertical column. Further, these sections, alone or in combination can make the sectioned vertical column is rotatable about the vertical axis. The boom apparatus can be coupled to one or more of these sections (e.g., at least one first movable section, at least one additional section, base section) for positioning of the x-ray source. Further, the least one intermediate section can be attached between the first movable section and base section or the least one intermediate section can be attached on an opposite side of the first movable section relative to the base section. In addition, the at least one first movable section and the at least one intermediate sections can be mounted within the base section and the base section has a vertical opening that allows vertical travel of the boom apparatus within the base section, or the first movable section and the at least one intermediate sections can be mounted outside the base section. In exemplary configurations, a boom transport mechanism can be actuable to provide vertical movement along at least a portion of the section to which the boom apparatus is attached.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, counterbalance apparatus 130 can be implemented in a number of ways, using a motor 88 or some other type of actuator that is optionally supplemented by tension force mechanism 104, such as a spring, as described previously. Boom apparatus 70 may use counterweight 80 or some other type of mechanical compensation for supporting its vertical displacement from one position to another. Additional sensors can be used for indicating the amount of force or pressure exerted by the operator and motion control logic may respond by changing column height more quickly or slowly based on sensor detection. Column height may also be automatically or manually adjusted as part of docking procedure when preparing mobile radiography unit 10 for transport. Sectioned vertical column 30 may have more than one movable section, using a ganged arrangement of telescoping sections, interconnected for mutual movement using additional pulleys or other conventional devices.

Thus, what is provided is an apparatus and method for column height adjustment in a mobile radiography apparatus having a collapsible support column with an x-ray boom of adjustable height.

What is claimed is:

1. A method for setting up a portable radiographic unit for an exposure, comprising:
    mounting a sectioned vertical column on a portable transport frame, wherein the column defines a vertical axis and comprises a base section having a fixed vertical position relative to the vertical axis and at least one movable section that is vertically translatable to extend the vertical column along the vertical axis;
    coupling a counterbalance apparatus to the at least one movable section of the vertical column, the counterbalance apparatus comprising an actuator that is energizable to translate the at least one movable section along the vertical axis;
    coupling a boom apparatus supporting an x-ray source to the at least one movable section for vertical displacement of the boom apparatus to a height position; and
    responding to an actuation instruction to adjust the height of the boom apparatus for the exposure by translating the at least one movable section of the vertical column along the vertical axis, where the boom apparatus is displaceable over a range of height settings along the movable section, and where translating the at least one movable section comprises changing the speed of translation according to proximity of the boom apparatus height to one of upper and lower boundaries of the range.

2. The method of claim 1 wherein the operator instruction indicates a type of radiographic image to be obtained.

3. The method of claim 1 wherein the operator instruction is entered at a keyboard.

4. The method of claim 1 wherein the operator instruction comprises urging the boom apparatus upward or downward.

5. The method of claim 1 further comprising obtaining a signal indicative of the height position of the boom apparatus.

6. The method of claim 1 further comprising obtaining a signal indicative of the height position of the vertical column.

7. The method of claim 6 wherein obtaining the signal comprises obtaining the signal from a linear encoder.

8. The method of claim 1 wherein coupling the boom apparatus to the at least one movable section comprises mounting the boom apparatus within a track.

9. The method of claim 1, comprising: adjusting the height of the vertical column for the exposure in response to upward or downward urging of the boom apparatus by an operator, wherein the boom apparatus is movably displaceable vertically over a range that extends along at least a portion of the movable section, wherein adjusting the height of the vertical column comprises compensating for the upward or downward urging to adjust the boom apparatus height toward the center of the range.

10. A method for setting up a portable radiographic unit for an exposure, comprising:
   mounting a sectioned vertical column on a portable transport frame, wherein the column defines a vertical axis and comprises a base section having a fixed vertical position relative to the vertical axis and at least one movable section that is vertically translatable to extend the vertical column along the vertical axis;
   coupling a counterbalance apparatus to the at least one movable section of the vertical column, the counterbalance apparatus comprising an actuator that is energizable to translate the at least one movable section along the vertical axis;
   coupling a boom apparatus supporting an x-ray source to the at least one movable section for vertical displacement of the boom apparatus to a height position;
   responding to an actuation to adjust the height of the boom apparatus for the exposure by translating the at least one movable section of the vertical column along the vertical axis; and
   adjusting the height of the vertical column for the exposure in response to upward or downward urging of the boom apparatus by an operator, where the boom apparatus is movably displaceable vertically over a range along at least a portion of the movable section, where adjusting the height of the vertical column comprises compensating for the upward or downward urging to adjust the boom apparatus height toward a center of the range.

* * * * *